(12) United States Patent
Baru et al.

(10) Patent No.: US 10,143,844 B2
(45) Date of Patent: Dec. 4, 2018

(54) NERVE STIMULATION SYSTEMS VIA ENDOVASCULAR LEADS

(71) Applicant: BIOTRONIK SE & Co. KG, Berlin (DE)

(72) Inventors: Marcelo Baru, Tualatin, OR (US); Dirk Muessig, West Linn, OR (US); Alan Fryer, Portland, OR (US)

(73) Assignee: BIOTRONIK SE & Co. KG (DE)

( * ) Notice: Subject to any disclaimer, the term of this patent is extended or adjusted under 35 U.S.C. 154(b) by 0 days.

(21) Appl. No.: 15/041,150

(22) Filed: Feb. 11, 2016

(65) Prior Publication Data

US 2016/0256687 A1    Sep. 8, 2016

Related U.S. Application Data

(60) Provisional application No. 62/127,296, filed on Mar. 3, 2015.

(51) Int. Cl.
*A61N 1/362* (2006.01)
*A61N 1/36* (2006.01)
(Continued)

(52) U.S. Cl.
CPC ........ *A61N 1/36139* (2013.01); *A61B 5/0826* (2013.01); *A61B 5/4836* (2013.01); *A61B 5/686* (2013.01); *A61N 1/056* (2013.01); *A61N 1/0558* (2013.01); *A61N 1/3601* (2013.01); *A61N 1/3611* (2013.01); *A61N 1/3627* (2013.01); *A61N 1/36053* (2013.01); *A61N 1/36114* (2013.01); *A61N 1/36135* (2013.01);
(Continued)

(58) Field of Classification Search
CPC .............. A61N 1/36053; A61N 1/3627; A61N 1/36114; A61N 1/0558; A61N 1/056; A61N 2005/1004
See application file for complete search history.

(56) References Cited

U.S. PATENT DOCUMENTS 7,146,226 B2 * 12/2006 Lau ................... A61F 2/2481
607/129
7,979,128 B2    7/2011  Tehrani et al.
(Continued)

FOREIGN PATENT DOCUMENTS

WO    WO 2008/092246 A1    8/2008

OTHER PUBLICATIONS

Bar-Cohen et al. "Novel use of a vascular plug to anchor an azygous vein ICD lead", *Journal of Cardiovascular Electrophysiology*, 21(1), 99-102, 2010.
(Continued)

*Primary Examiner* — Alyssa M Alter
(74) *Attorney, Agent, or Firm* — Craig A. Fieschko, Esq.; Dewitt Ross & Stevens S.C.

(57) ABSTRACT

An implantable stimulation system includes a pulse generator having at least one implantable lead (200) with a proximal end (301) electrically connected to the pulse generator, and a distal end bearing at least one stimulation electrode (201.1, 201.2) electrically connected to the proximal end (301), and thus to the pulse generator. The distal end of the lead (200) includes at least one expandable member (202) configured to laterally extend from the lead (200) in its expanded state, and that carries the stimulation electrode(s) (201.1, 201.2).

19 Claims, 10 Drawing Sheets

(51) Int. Cl.
*A61B 5/08* (2006.01)
*A61N 1/372* (2006.01)
*A61N 1/05* (2006.01)
*A61N 1/365* (2006.01)
*A61B 5/00* (2006.01)
*A61B 5/11* (2006.01)

(52) U.S. Cl.
CPC ...... *A61N 1/36514* (2013.01); *A61N 1/37211* (2013.01); *A61B 5/0031* (2013.01); *A61B 5/0809* (2013.01); *A61B 5/1116* (2013.01); *A61B 2562/0219* (2013.01)

(56) References Cited

U.S. PATENT DOCUMENTS

| | | | |
|---|---|---|---|
| 8,419,645 | B2 | 4/2013 | Lian et al. |
| 8,433,412 | B1 | 4/2013 | Westlund et al. |
| 8,571,662 | B2 | 10/2013 | Hoffer |
| 8,630,704 | B2 | 1/2014 | Pu et al. |
| 9,026,231 | B2 | 5/2015 | Hoffer |
| 9,108,058 | B2 | 8/2015 | Hoffer |
| 9,108,059 | B2 | 8/2015 | Hoffer |
| 9,168,377 | B2 | 10/2015 | Hoffer |
| 9,220,898 | B2 | 12/2015 | Hoffer |
| 2005/0085866 | A1 | 4/2005 | Tehrani |
| 2006/0155341 | A1 | 7/2006 | Tehrani et al. |
| 2006/0206154 | A1* | 9/2006 | Moffitt ............... A61N 1/3627 607/9 |
| 2010/0036451 | A1 | 2/2010 | Hoffer |
| 2013/0116743 | A1 | 5/2013 | Karamanoglu et al. |
| 2014/0039286 | A1 | 2/2014 | Hoffer |
| 2014/0067032 | A1 | 3/2014 | Morris et al. |
| 2014/0343632 | A1 | 11/2014 | Hoffer |
| 2014/0343635 | A1 | 11/2014 | Hoffer |
| 2014/0343636 | A1 | 11/2014 | Hoffer |
| 2015/0012070 | A1 | 1/2015 | Hoffer |
| 2015/0306397 | A1 | 10/2015 | Hoffer |

OTHER PUBLICATIONS

Escher et al. "Clinical control of respiration by transvenous phrenic pacing", *Trans. Amer. Soc. Artif. Int. Organs*, vol. XIV, 192-197, 1968.
Hasdemir et al. "Endovascular stimulation of autonomic neural elements in the superior vena cava using a flexible loop catheter", *Japanese Heart Journal*, 44(3), 417-27, 2003.
http://circ.ahajournals.org/content/117/20/2608 abstract.
http://www.ncbi.nlm.nih.gov/pmc/articles/PMC3493802/.
Karceski, "Vagus nerve stimulation therapy", *UptoDate Review*, 2011.
Rendón et al. "Mapping the Human Body for Vibrations using an Accelerometer", *Proceedings of the 29th Annual IEEE EMBS International Conference*, FrA06.1, pp. 1671-1674, 2007.
Thompson et al. "Bradycardia induced by intravascular versus direct stimulation of the vagus nerve", *Annals of Thoracic Surgery*, 65(3), 637-42, 1998.
European Search Report, 16154006.7-1666, dated Jul. 27, 2016.

* cited by examiner

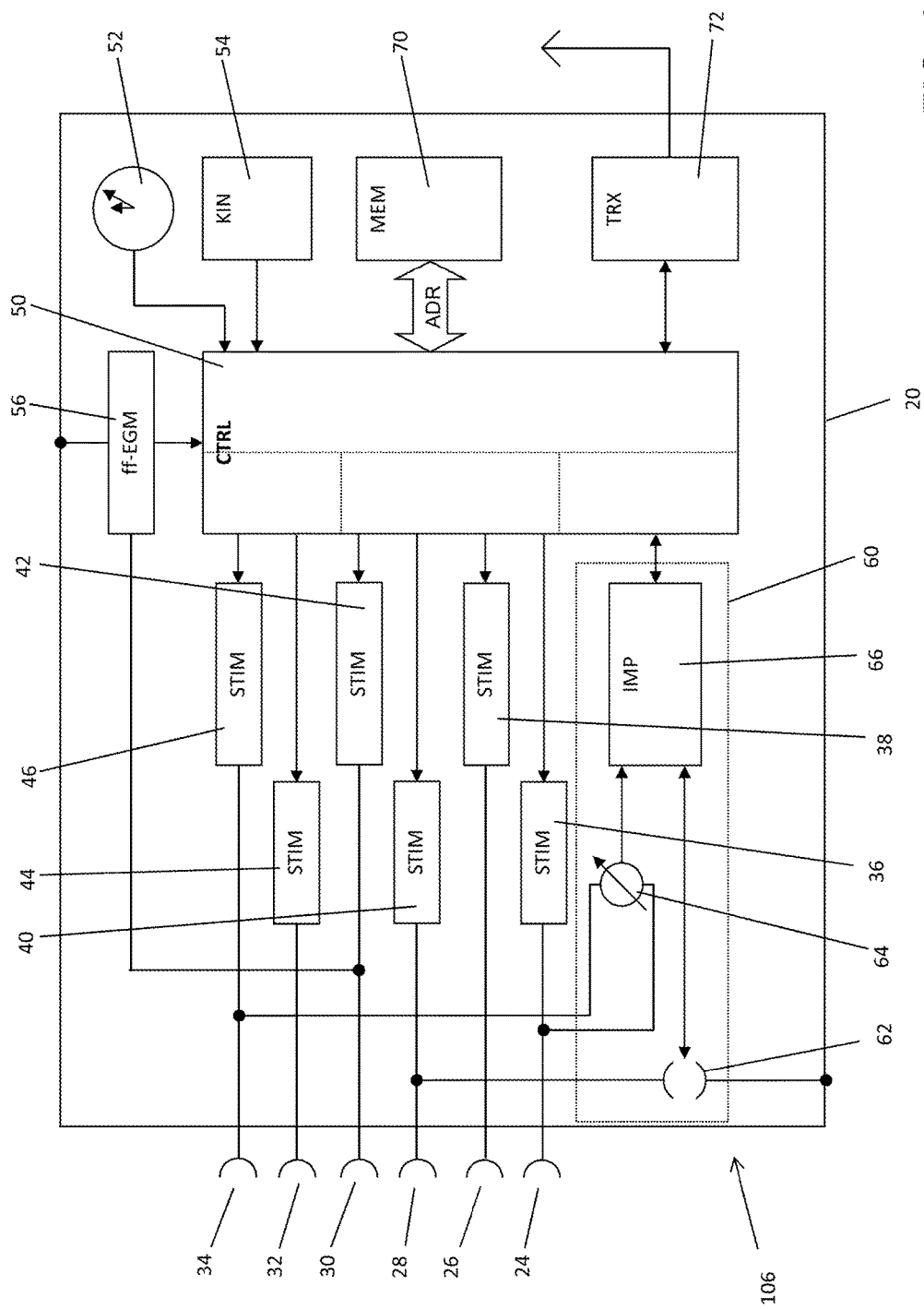

NERVE STIMULATION SYSTEMS VIA ENDOVASCULAR LEADS

CROSS-REFERENCE TO RELATED APPLICATIONS

This application claims priority under 35 USC § 119(e) to U.S. Provisional Patent Application 62/127,296 filed 3 Mar. 2015, the entirety of which is incorporated by reference herein.

FIELD OF THE INVENTION

The invention relates to implantable stimulation systems including an implantable pulse generator (IPG) including a connected stimulation lead having at least one stimulation electrode for delivery of stimulation pulses. The systems are suitable for Vagus-Phrenic Nerve Stimulation (VNS-PhrNS) therapy, in particular for the treatment of patients suffering from Congestive Heart Failure (CHF) with Central Sleep Apnea (CSA) syndrome.

BACKGROUND OF THE INVENTION

Transvascular stimulation of a vagus nerve via a catheter, for the purpose of heart rate reduction (parasympathetic drive), was first reported by Thompson et al. in 1998 [Thompson et al. "Bradycardia induced by intravascular versus direct stimulation of the vagus nerve", Annals of Thoracic Surgery, 65 (3), 637-42, 1998]. A few years later, Hasdemir et al. [Hasdemir et al. "Endovascular stimulation of autonomic neural elements in the superior vena cava using a flexible loop catheter", Japanese Heart Journal, 44 (3), 417-27, 2003] investigated the use of a flexible loop with multiple contacts in the superior vena cava (SVC). This work showed stimulation at anterior sites resulted in phrenic nerve stimulation, whereas posterior site stimulation affected sinus cycle length and atrioventricular conduction while avoiding phrenic nerve stimulation.

Transvascular stimulation of the phrenic nerves, on the other hand, dates back to the 1950s [Doris J. W. Escher et al. "Clinical control of respiration by transvenous phrenic pacing", Trans. Amer. Soc. Artif. Int. Organs, Vol. XIV, 192-197, 1968]. WO2008/092246 A1 discloses a stimulation device with a single endovascular lead having multiple electrodes for stimulation of a vagus nerve and/or a phrenic nerve. The reference describes phrenic nerve stimulation to regulate breathing, and fine-tuning the positioning of the electrode array in the internal jugular vein (IJV) by observing the patient's breathing.

U.S. Pat. No. 8,433,412 B1 discloses a lead-electrode system for use with an Implantable Medical Device (IMD) configured to monitor and/or treat both cardiac and respiratory conditions. More particularly, versions of the invention relate to a lead-electrode configuration of a combination IMD that combines therapies such as cardiac pacing, respiratory sensing, phrenic nerve stimulation, defibrillation, and/or biventricular pacing, referred to as Cardiac Resynchronization Therapy (CRT). Stimulation and/or sensing leads may be placed in a small pericardiophrenic vein, a brachiocephalic vein, an azygos vein, a thoracic intercostal vein, or other thoracic vein that affords proximity to the phrenic nerve for stimulation. Respiration sensing may be performed via transthoracic impedance.

US 20140067032 A1 discloses an implantable medical system including an electrode-bearing lead that is implanted through the lumen wall of a blood vessel located adjacent to a target nerve, in particular a vagus nerve, with the lead including an anchor configured to secure the lead (and thereby the electrode) to tissue outside of the vessel near the target nerve.

U.S. Pat. No. 8,630,704 B2 discloses utilizing measurement of respiratory stability or instability during sleep or rest as a feedback to control stimulation of an autonomic neural target (e.g., vagus nerve stimulation).

Vagus nerve stimulation recently emerged as a potential progression-preventing and treatment option for CHF patients. Experimental data have demonstrated that stimulation of a vagus nerve at the cervical level is able to reverse ventricular remodeling of the failing heart. There is also evidence that increasing parasympathetic activity may stimulate the production of nitric oxide, and reduce the devastating inflammatory process involved in heart failure. Present vagus nerve stimulation devices for CHF involve an implanted nerve cuff electrode that connects via wires to an IPG in the patient's chest. A standard pacemaker sensing lead in the ventricle has been proposed in prior art for the purpose of synchronous delivery of vagus nerve stimulation pulses in the cardiac refractory period, although other prior art devices operate asynchronously to the cardiac cycle. Stimulation of both the right and left vagus nerves are disclosed in prior art for CHF treatment.

Implantations of nerve cuff electrodes require accessing and exposing the nerve. A drawback of such implantation is that the shape, size, thickness, orientation, flexibility, and associated leadout cables of the electrodes must carefully match the anatomical site to avoid nerve damage. A less invasive approach is preferred for cervical VNS, in particular one that can employ a lead implantable via well-established pacemaker-implantation techniques which avoid the need for additional physician training.

Another fact to consider is that almost half of the Congestive Heart Failure (CHF) patient population suffers from Central Sleep Apnea (CSA). Although CRT has become the standard device therapy for the treatment of NYHA class III or IV heart failure patients with left ventricular ejection fractions (LVEF)≤35% and QRS≥130 ms, only 7% of all eligible CHF patients receive the device (see http://www.ncbi.nlm.nih.gov/pmc/articles/PMC3493802/), and approximately 30% of those who receive it are classified as non-responders (see http://circ.ahajournals.org/content/117/20/2608. abstract). Hence, a combination device as proposed by U.S. Pat. No. 8,433,412 B1 is not optimal for the treatment of CHF with CSA.

Central sleep apnea (CSA) can be managed/treated via phrenic nerve stimulation (PhrNS). However, these nerves are too fragile for nerve cuff electrodes. U.S. Pat. No. 8,433,412 B1 discloses an "implantable respiration lead" for transvascular stimulation of a phrenic nerve via installation in a pericardiophrenic vein, a brachiocephalic vein, an internal jugular vein (IJV), a superior intercostal vein, the superior vena cava (SVC), or other appropriate locations.

Transvascular stimulation of a nerve is appealing because the implantation of endovascular leads is well known by physicians dealing with CHF patients. The vascular system contains numerous locations in which are in close proximity to vagus and phrenic nerves. However, chronically implanting a lead in a large, easily accessible vein as proposed by WO2008/092246 A1 requires a suitable anchoring solution not described in that reference. Furthermore, electrode structures as proposed by WO2008/092246 A1 may be prone to blood clot formation, and thus are preferably avoided for chronic implantation.

SUMMARY OF THE INVENTION

The invention seeks to provide a nerve stimulation device that advances the management/treatment of Congestive Heart Failure (CHF) patients, in particular those who also suffer from Central Sleep Apnea (CSA) syndrome.

The invention also seeks to provide a dual-purpose implantable system for Vagus-Phrenic Nerve Stimulation (VNS-PhrNS) based on an implantable pulse generator (IPG) preferably having a single endovascular lead, the system being particularly suitable for CHF patients with CSA syndrome, and suitable for integration into a Home Monitoring/Remote Programming therapy regime.

A preferred version of the invention involves an implantable nerve stimulation system including an IPG, and an implantable lead having a proximal end electrically connected to the IPG and a distal end having at least one stimulation electrode. The distal lead end has an expandable member configured to laterally extend from the lead in its expanded state, and which carries the stimulation electrode(s).

The implantable nerve stimulation system enables stimulation methods using endovascular multi-electrode leads implanted through typical vascular access sites for pacemaker leads, situated in vessels at suitable spots for nerve stimulation, and anchored to the vessel walls by the expandable member. The expandable member (e.g., a thin disk of silicone or other insulating material) preferably springs outwardly once the lead is unsheathed from its introducer, with the electrode(s) being located on the expandable member to face the target nerve when the lead is deployed, thereby providing directionality for stimulation purposes.

The invention addresses the prior art's lack of suitable solutions for anchoring endovascular leads in large, easily accessible veins. In particular, the absence of data supporting the safety and efficacy of SVC filters for upper-extremity Deep Vein Thrombosis (DVT) [http://www.ncbi.nlm.nih.gov/pmc/articles/PMC3493802/] have precluded the chronic implantation of endovascular leads in large veins for the purpose of nerve stimulation using stent-type electrodes. On the other hand, pre-shaped electrodes and the like are prone to migration issues during chronic implantation.

The invention also avoids unintended co-stimulation of nerves. Co-stimulation of the phrenic nerve, for example, is one of the reported side effects in helical-spiral-cuff-based VNS for epilepsy management [Karceski "Vagus nerve stimulation therapy", UptoDate Review, 2011]. Some patients experience uncomfortable spasming of the left chest wall due to collateral spread of stimulation to the phrenic nerve, causing contraction of the left hemi diaphragm. Contraction of the left anterior sternocleidomastoid muscle may also occur owing to stimulation of adjacent structures. These symptoms are often precipitated by the patient's assumption of certain postures or movement, and are relieved by changing position. Hence, a lead with electrodes that is implanted through the lumen wall of an IJV as described in US 20140067032 A1 may suffer from spillage to the adjacent phrenic nerve when utilized for VNS.

The invention provides a feasible anchoring solution for the implantation of endovascular leads in a vessel for nerve stimulation in a manner that minimizes spillage to adjacent tissue. It is particularly suitable for vagus nerve stimulation (VNS) for the management/treatment of CHF, for phrenic nerve stimulation (PhrNS) for central sleep apnea (CSA), and for breathing assistance/control in patients with partial or complete respiratory insufficiency, e.g. chronic obstructive pulmonary disease (COPD) or quadriplegia.

A preferred version of the system includes a single endovascular multi-electrode lead that gets implanted through a subclavian vein, travels up the lumen of an internal jugular vein (IJV), and crosses the IJV lumen wall at a spot where the nearby vagus nerve can be recruited. The distal end of the lead terminates in an insulating expandable member (e.g. a thin silicone disk) that springs outwardly once the lead is unsheathed from its introducer. This insulating expandable member works as an anchor which prevents lead dislodgement following vein puncture and introducer retrieval, and which hosts the electrodes to provide directionality of the electrical field towards the target nerve, thus minimizing unwanted stimulation of adjacent tissue.

In a preferred version of the present invention, the distal end of the endovascular multi-electrode lead of the implantable stimulation system is configured to puncture the wall of a vessel, thereby piercing through the vessel wall. Electrical mapping of a suitable puncturing spot may be assisted by a non-invasive imaging technique (e.g. fluoroscopy or ultrasound). The expandable member is configured such that it serves as an anchor via the expandable member in its expanded state, anchoring the distal end of the lead in the vessel wall.

In this version, the proximal end of the endovascular lead connects to an implantable pulse generator (IPG) located in a pocket in the patient's chest. The IPG can perform intrathoracic far-field electrogram (ff-EGM) recordings for heart rate and CHF monitoring. It may also include a tilt (inclination) sensor, which can be combined with electrical impedance plethysmography (via an extra electrode on the lead and one of the electrodes on the anchoring expandable member described above) to obtain a signal corresponding to the pressure waveforms in the IJV and common carotid artery (CCA). The IPG may also communicate via a MICS-band link to an external Programmer, and/or to a bedside Patient Messenger connected to a Home Monitoring/Remote Programming Center.

The endovascular lead may also or instead be implanted to target phrenic nerve stimulation (PhrNS) for applications such as management/treatment of central sleep apnea (CSA), and/or assisting/controlling breathing in patients with partial or complete respiratory insufficiency, e.g. chronic obstructive pulmonary disease (COPD) or quadriplegia. Here the IPG may include a kinematic sensor for extraction of a Respiration Effort Signal (REFFS) to be used for detecting hypopnea and apnea conditions in CSA. Upon detection of one of these conditions, PhrNS can be delivered to restore normal breathing.

Preferably, the pulse generator is configured to deliver VNS and/or PhrNS depending on the REFFS. Single or dual-lead VNS-PhrNS can be used for patients suffering from CHF with CSA. REFFS may also be used as a feed-forward parameter for the delivery of VNS and/or PhrNS therapies. If VNS is to be delivered, this feed-forward operation will cause any stimulation spillage to the phrenic nerve (should it occur) to assist with breathing. If PhrNS is to be delivered, this feed-forward operation can also assist with breathing, e.g., when the patient is hospitalized and placed on mechanical ventilation. Bilateral implantations and different combinations of VNS and PhrNS allow treatment of different conditions.

The system can include a cardiac stimulation lead in the form of a right ventricular lead with a floating atrial electrode, and having associated VDD pacemaker circuitry in the IPG. This allows atrial fibrillation (AF) monitoring, monitoring of PR interval for autonomic tone, and delivery of nerve stimulation synchronized with atrial or ventricular events. Ventricular pacing can also be provided as a safety feature.

The invention can be utilized for unilateral/bilateral vagus nerve stimulation (VNS) for the management/treatment of congestive heart failure (CHF) patients; phrenic nerve stimulation (PhrNS) for the treatment of central sleep apnea (CSA) patients, or for assisting/controlling breathing in patients with partial or complete respiratory insufficiency, e.g. chronic obstructive pulmonary disease (COPD) or quadriplegia; or for combinations thereof. It can also support VDD pacing via a separate lead that goes into the heart. The IPG can be configured to suit a particular one or a combination of these applications.

Each vagus nerve is situated posteriorly between the common carotid artery (CCA) and the internal jugular vein (IJV) in the carotid sheath, a fibrous connective tissue that surrounds the vascular compartment of the neck. The vagus nerves run parallel to the IJVs. The distance from the vagus nerve to the IJV is typically in the range of 2 mm to 10 mm. The phrenic nerves also run parallel to the IJVs at a similar distance but on the opposite sides.

Either IJV can be easily accessed via the subclavian veins, which are typically used as access sites for the implantation of pacemaker leads. When implementing the invention, a vagus nerve stimulation (VNS) lead can be inserted through a subclavian vein and routed upwardly through the lumen of an IJV. The lead introducer might perform transvascular electro-anatomical mapping for the purpose of determining a suitable location for VNS. Such mapping may be assisted by the use of non-invasive imaging techniques, such as fluoroscopy or ultrasound.

Once a suitable location is transvascularly identified, an introducer for the lead can puncture the IJV to allow the lead to cross the IJV lumen wall. An insulating expandable member (e.g. a thin silicone disk) on the lead springs outwardly once the lead is unsheathed, preventing the lead from dislodging once the introducer is retrieved. At least two electrodes are present on the insulating expandable member to perform VNS. The VNS lead proximal end, on the other hand, is tunneled subcutaneously and connected to the implantable pulse generator (IPG), which is implanted in a pocket in the patient's chest.

A similar lead and implant procedure can be used for phrenic nerve stimulation (PhrNS). PhrNS can be used for the management/treatment of central sleep apnea (CSA) or for assisting/controlling breathing in patients with partial or complete respiratory insufficiency, e.g., bilateral PhrNS could be used to treat chronic obstructive pulmonary disease (COPD) or quadriplegic patients. Bilateral VNS is also possible, as well as different VNS-PhrNS combinations for different conditions.

Although the IPG can record a far-field electrogram (ff-EGM) utilizing a vector between an electrode in the lead and the IPG case, which can be utilized for heart rate determination (e.g. to assess VNS effect) and heart condition monitoring in congestive heart failure (CHF), the systems and methods of the present invention are compatible and can support a right ventricle lead with a floating atrial contact to provide VDD pacing. This pacemaker-type lead allows monitoring for paroxysmal or persistent atrial fibrillation (AF), drug efficacy in AF treatment, PR interval for autonomic tone, while also allowing delivering synchronized nerve stimulation with atrial or ventricular events. It can also provide ventricular pacing as a safety feature.

The IPG may also include a tilt (inclination) sensor, preferably in the form of a triaxial accelerometer. This sensor permits monitoring sleeping positions at night time. This statistic is of particular interest because patients with CHF generally tend to sleep in a sitting position due to breathing difficulties (as their lungs fill with fluid). The pulse generator of the implantable stimulation system might then be configured to record vascular pressure waveforms depending on the tilt signal and the far field electrogram. Given the proximity of the VNS implanted lead to the IJV and CCA, impedance plethsymography utilizing the lead's electrodes can indirectly measure the combined pressure waveforms of both vessels. Such a combined pressure waveform can be further decomposed into the individual CCA and IJV pressure waveforms based on the patient posture determined by the tilt sensor. In the supine position, the IJV is partially distended and its higher compliance with respect to the CCA provides a waveform that reflects the IJV pressure. On the other hand, in semi-recumbent and erect postures, the IJV vein normally collapses to a slit-like passage, and the CCA volume pulsation waveform is predominant.

Alternatively or additionally, a pressure/pulsation sensor may be embedded in the distal end of the lead to perform pressure recording instead of impedance plethysmography. A triaxial accelerometer, or other pressure/pulsation sensors as described in other prior references noted in this document, can be used for pressure recording.

The IPG may also derive a Respiration Effort Signal (REFFS) from a kinematic sensor, preferably from the triaxial accelerometer or other tilt sensor (where provided). REFFS may be used as a feed-forward parameter for managing any VNS spillage to the phrenic nerve so that VNS assists with breathing (via PhrNS) rather than interfering with it, given both VNS and PhrNS utilize similar stimulation patterns. Preferably, VNS therapy is delivered during the breathing pause phase derived from REFFS.

REFFS can also be utilized to detect hypopnea and apnea conditions in CSA patients, and to deliver PhrNS accordingly to re-establish normal breathing. Monitoring and detection of apnea events is preferably performed independently of the time of day, as apneas can occur at any time of day if the patient falls asleep. Upon detection of a hypopnea (shallow breathing effort) or an apnea (absence of breathing) condition from REFFS, PhrNS therapy may be delivered to re-establish normal breathing. Although PhrNS spillage to the vagus nerve may be avoided due to the distance between the vagus and phrenic nerves at the target site, and/or owing to the preferred lead configuration (as described in this document), spillage is actually beneficial for CHF as both are in the same frequency range.

Data from the different IPG sensors mentioned above can be utilized to analyze improvement or worsening of a patient's condition. Such info can be telemetered via a MICS link to a bedside Patient Messenger in communication with a Home Monitoring/Remote Programming Center. The same wireless link can be used for IPG programming via an external Programmer.

BRIEF DESCRIPTION OF THE DRAWINGS

FIG. 10 is a schematic diagram of selected components of the implantable pulse generator.

DETAILED DESCRIPTION OF EXEMPLARY VERSIONS OF THE INVENTION

Figure 1:
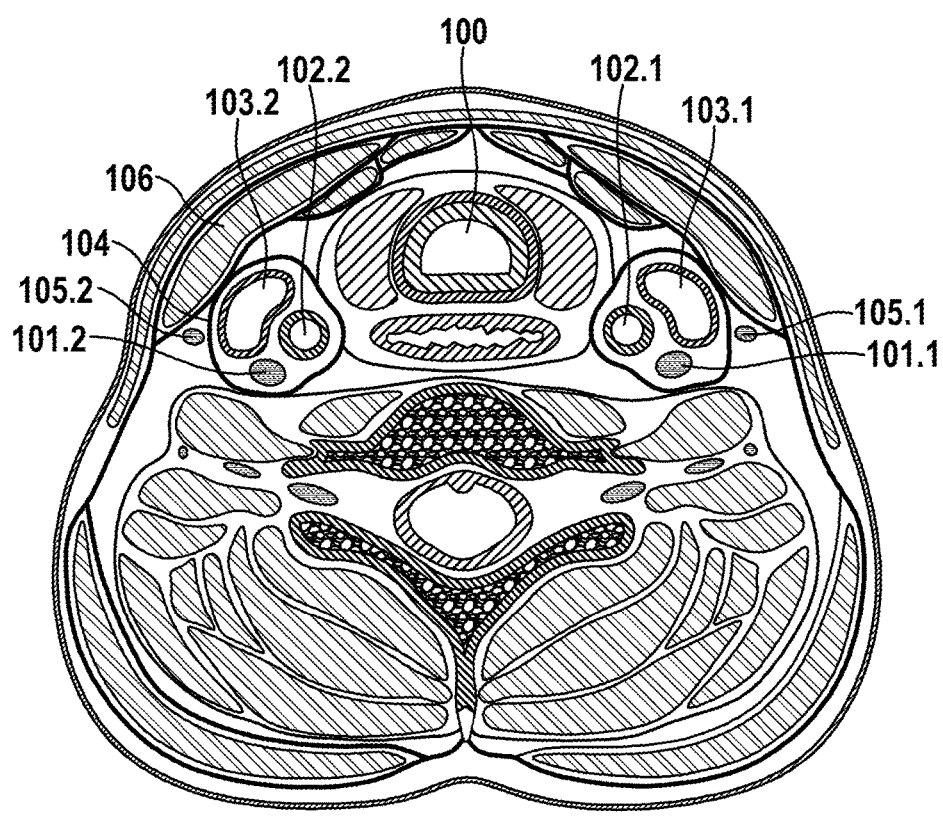
FIG. 1 shows a cross-sectional drawing of the human neck anatomy.

FIG. 1 shows a cross-sectional drawing of the human neck anatomy where element 100 represents the trachea. Each vagus nerve 101 is situated posteriorly between a common carotid artery (CCA) 102 and an internal jugular vein (IJV) 103 in a carotid sheath 104. The latter is a column of fascia that surrounds these elements 101, 102, and 103 as they pass through the neck. The phrenic nerves 105 also run adjacent to the IJVs 103, and the minimum distance to the corresponding vagus nerve 101 is in the order of 15 mm. This separation allows for a degree of stimulation selectivity between the two nerves 101 and 105. Element 106 represents the sternoclaidomastoid muscle.

Figure 2:
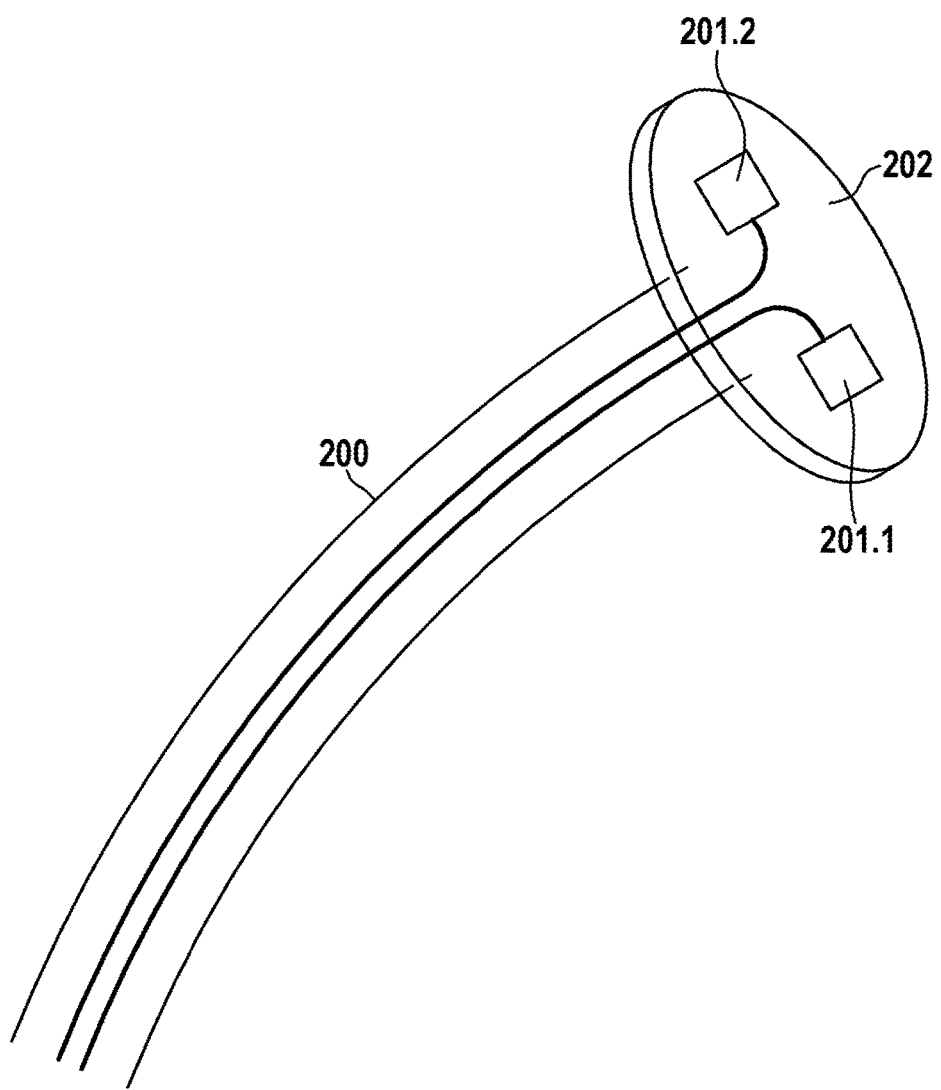
FIG. 2 shows an exemplary lead for use in the invention.

FIG. 2 shows a preferred version of the lead 200 of the present invention. The lead 200 includes at least two electrodes 201.1 and 201.2 (collectively referred to as electrodes 201), which are made of Pt/Ir or equivalent material and are situated on the insulating expandable member 202 such that they are exposed on only one side of the expandable member 202. The expandable member 202 is made of silicone or other resilient insulating material, and is self-expanding such that it springs outwardly once the lead 200 is unsheathed from its introducer. The lead 200 may be provided to a physician or other installer pre-assembled inside a suitable biocompatible introducer for implantation, i.e. a catheter and/or guide wire. Once the lead 200 is deployed, the expandable member 202 acts as an anchor for preventing the lead 200 from dislodging through the vessel wall, as further discussed below. The insulating characteristics of the expandable member 202 provide some degree of electrical insulation, directing the electrical field caused by stimulation towards the target nerve(s).

Figure 3:
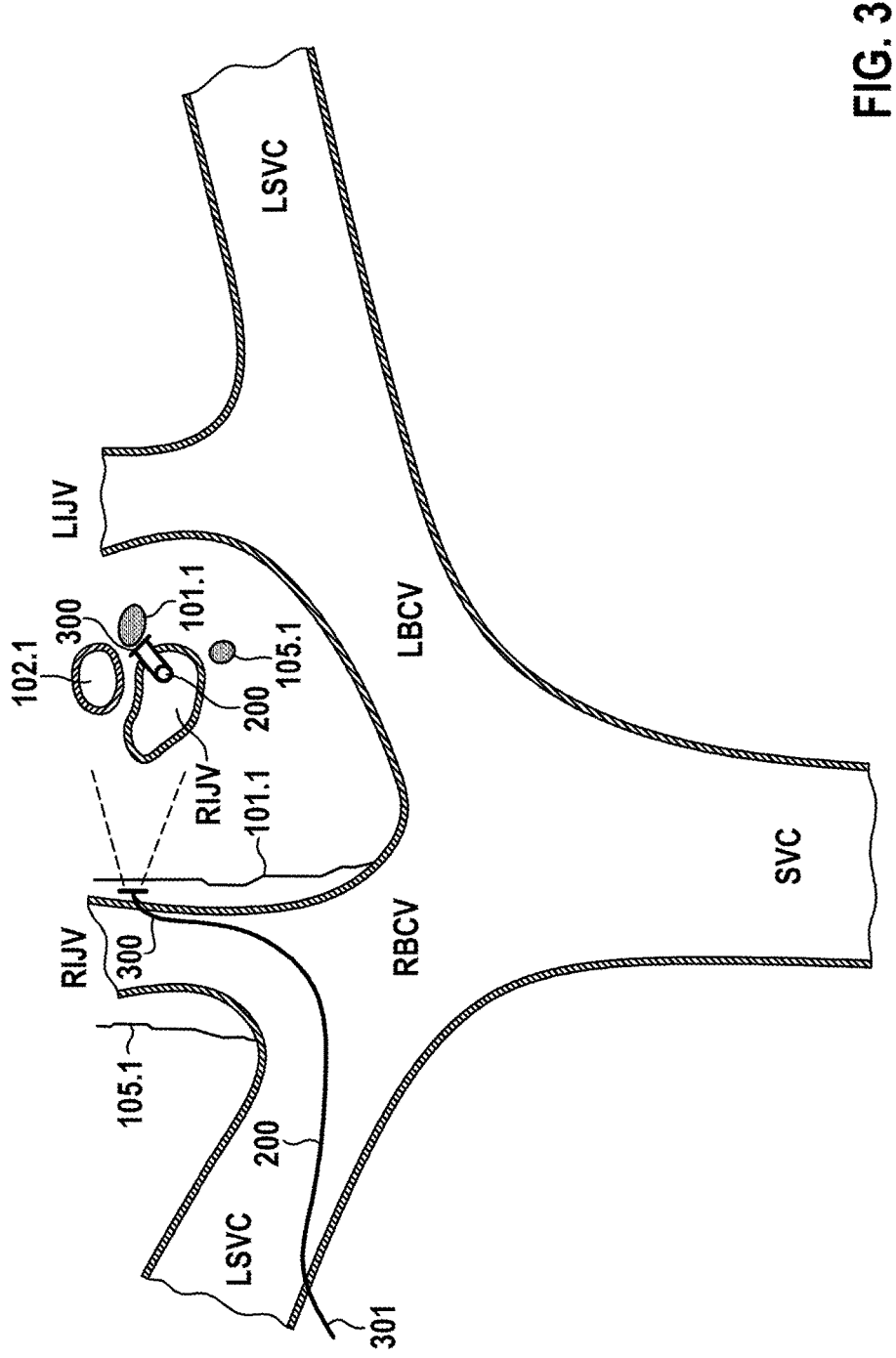
FIG. 3 illustrates exemplary lead placement for right vagus nerve stimulation (VNS), wherein the lead is inserted via the right subclavian vein (RSCV)

For right vagus nerve stimulation (VNS), the lead 200 is inserted via the right subclavian vein (RSCV) following a typical pacemaker-lead implant procedure, and is advanced upstream via the lumen of the right IJV (RIJV) as shown in FIG. 3. The lead 200 introducer (not shown) allows for transvascular electrical-anatomical mapping of the vagus nerve 101 via the RIJV wall. Mapping may involve searching for a spot 300 where a heart rate decrease (of a few beats per minute) can be triggered via electrical stimulation with minimal recruitment of the laryngeal muscles and other adjacent structures. A temporary external or minimally-invasive sensor, or a combination thereof, can be positioned in the region of the larynx for sensing evoked laryngeal activation. Examples of sensors include motion sensors (e.g. an accelerometer or strain gauge), an acoustical sensor (e.g. a microphone), or an electromyography (EMG) amplifier. Fluoroscopy and ultrasound imaging may assist with implantation to help visualize, for example, the location of the common carotid artery (CCA) 102.1.

Figure 4:
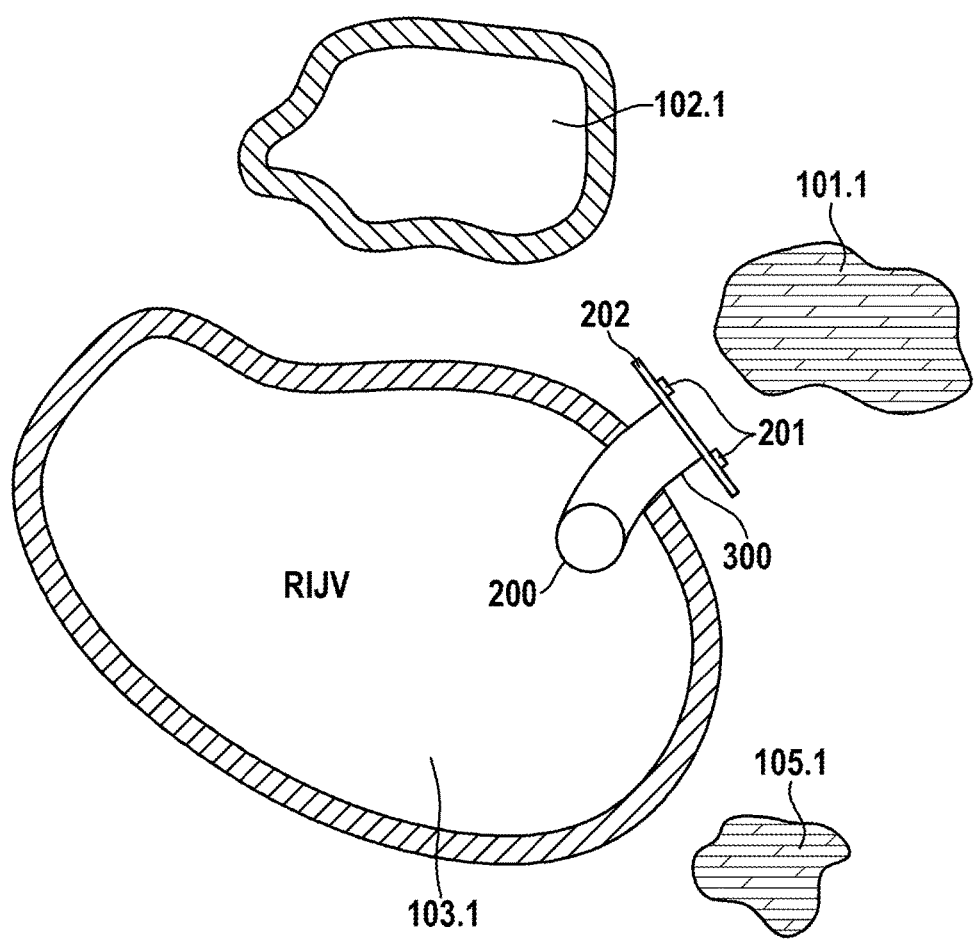
FIG. 4 schematically depicts an enlarged view of the anchored lead in FIG. 3.

When a suitable spot 300 is transvascularly identified via electrical mapping, the introducer punctures the RIJV (103.1) lumen wall to advance the tip of the lead 200 to the vicinity of the vagus nerve 101.1. Re-mapping can be performed to confirm recruitment of the vagus nerve 101.1. The enlarged view of FIG. 4 (not to scale) shows a schematic representation of the anchored lead 200 at spot 300. Once the introducer is removed, the expanded insulating member 202 on the lead 200 will prevent the lead 200 from dislodging. The electrodes 201 on the expandable member 202 will face the vagus nerve 101.1. The lead 200 can be rotated prior to introducer removal to achieve longitudinal or transverse stimulation of the vagus nerve 101.1 as desired. Scar tissue will form at the puncture site 300 in a similar way as if the lead 200 had been implanted as a regular pacemaker lead (i.e., from the outside into the vein). The proximal end 301 (see FIG. 3) of the lead 200 is routed subcutaneously to an implantable pulse generator (IPG), which is preferably implanted in a pocket in the patient's chest.

Figure 5B:
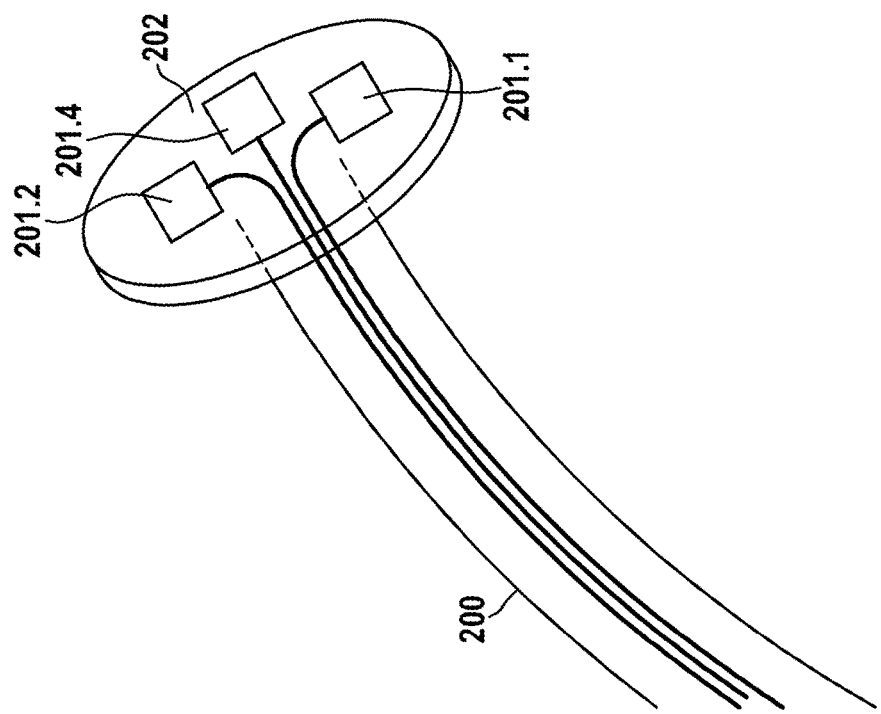
FIGS. 5A and B illustrate an alternative version of the lead.
Figure 5A:
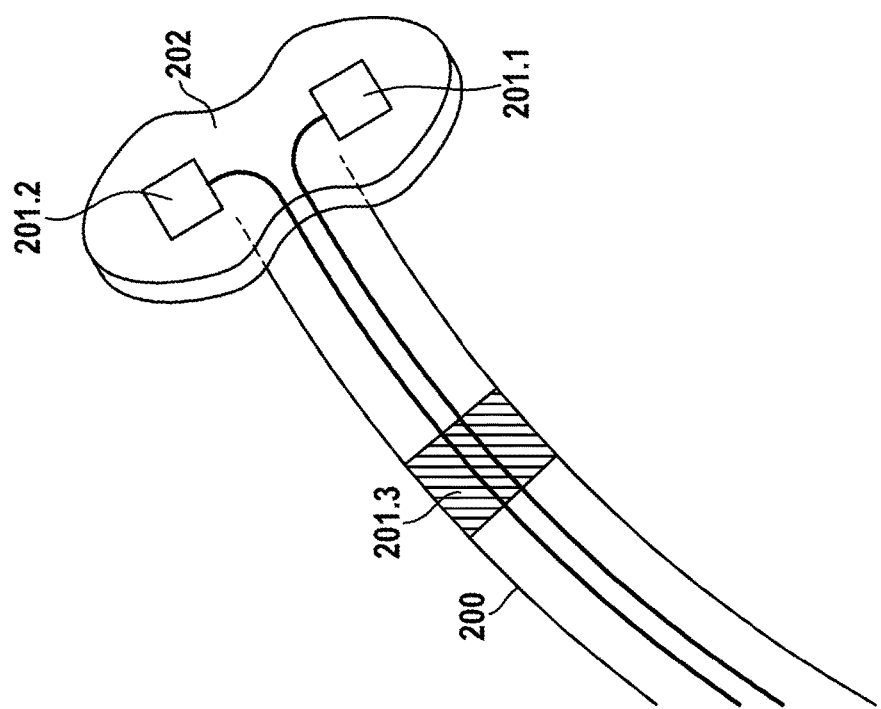

Several alternative constructions are possible for the lead 200. In a preferred alternative version shown in FIG. 5A, the expandable member 202 has a dual-lobed "8" shape instead of being circular/disc-like, as in FIG. 2. Instead of being formed as a unitary expandable member 202 with multiple lobes, the separate lobes might be provided on separate expandable members. At least one additional lead electrode 201.3 may be present on the lead 200 for purposes other than nerve stimulation, e.g., to perform impedance plethysmography. Such a lead electrode(s) 201.3 may be located inside or outside the lumen of the RIJV (103.1) after implantation.

In yet another version of the lead 200 (shown in FIG. 5B), three electrodes 201.1, 201.2, and 201.4 are hosted on the anchoring expandable member 202, and are arranged to permit guarded cathode stimulation to further concentrate the electrical field towards the vagus nerve 101.1.

Vagus nerve stimulation (VNS) therapy preferably consists of a programmable train of pulses with fixed charge per pulse and fixed frequency between pulses, delivered synchronously or asynchronously with the cardiac cycle. A far-field electrogram (ff-EGM), an example of which is shown in FIG. 2, may be used for synchronous delivery of VNS pulses (e.g., VNS pulses may be delivered after a programmable delay following an R-wave sensed event), and also for monitoring heart rate reduction caused by VNS. Preferably, the far-field electrogram (ff-EGM) 604 is recorded between the IPG case and an electrode 201 on the lead 200, or between an electrode 201 and another contact located in a subcutaneous lead connected to the IPG and implanted towards the heart.

Figure 6:
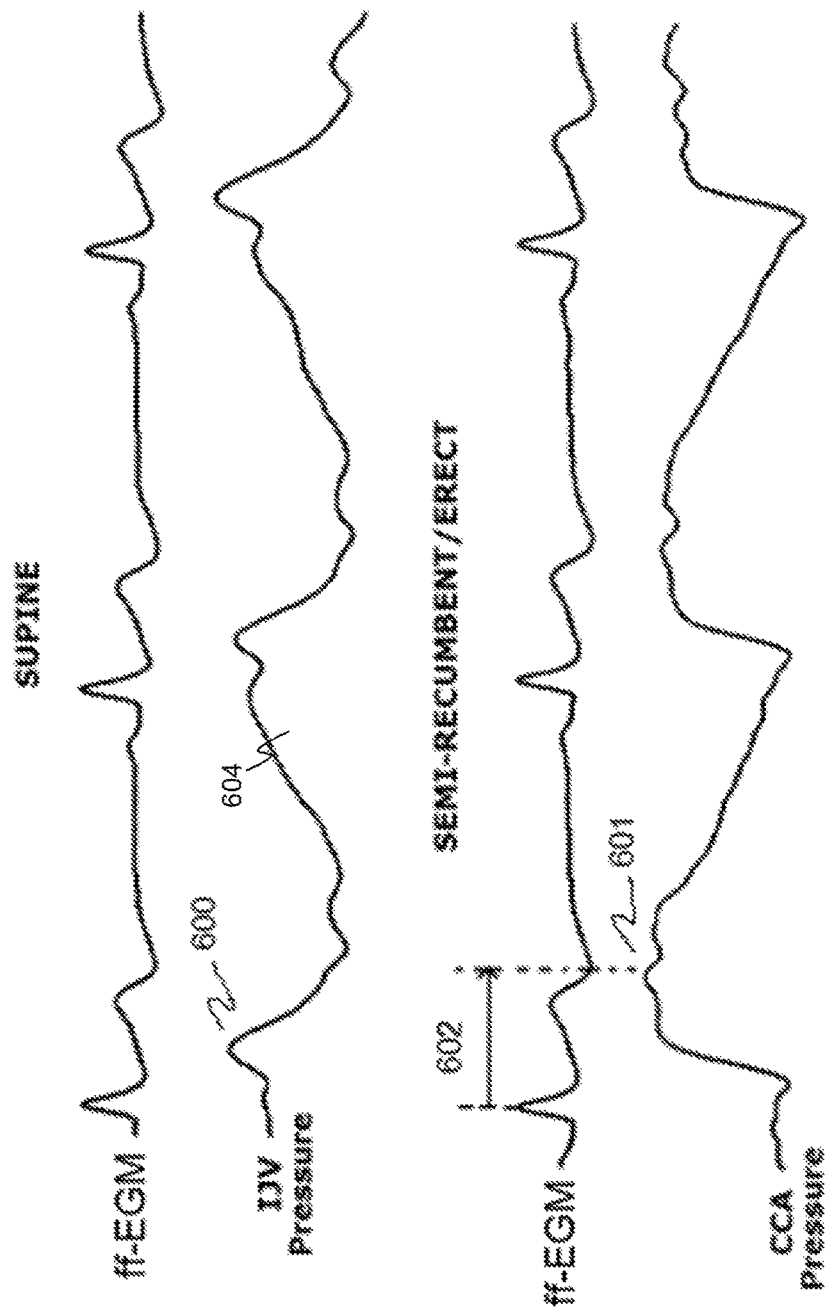
FIG. 6 illustrates CCA and IJV pressure waveforms, based on patient posture as determined by a tilt sensor, relative to a ff-EGM.

The IPG may also include a tilt (inclination) sensor, which preferably takes the form of a triaxial accelerometer. Given the location of the lead 200 relative to an internal jugular vein (IJV) and common carotid artery (CCA), impedance plethysmography between lead electrodes—for example, between 201.3 and either 201.1 or 201.2—provides a waveform representative of arterial and venous pressures in terms of shape and timing with respect to the cardiac cycle, and thus can be considered an indirect pressure waveform. Such a pressure waveform can be decomposed into the individual CCA and IJV pressure waveforms based on patient posture determined by the tilt sensor, as shown in FIG. 6.

In the supine position, the IJV is partially distended, and its higher compliance with respect to the CCA provides a waveform that reflects the IJV pressure. On the other hand, in semi-recumbent and erect postures, the IJV vein normally collapses to a slit-like passage leaving only the CCA volume pulsations. Rather than synchronizing VNS pulses with R-wave events or other EGM waveform characteristics, VNS pulses may instead be delivered synchronously with pressure peaks 600 and 601.

The IJV and CCA pressure waveforms provide relevant information about the patient's heart condition, and are therefore very useful for the monitoring of congestive heart failure (CHF). As mentioned, the IJV pressure waveform can be differentiated from the CCA pressure waveform by determining when the tilt sensor indicates a supine position or a semirecumbent or erect position, respectively. The sampled pressure waveform is band-pass filtered to eliminate or minimize respiratory components. Preferably, the lower limit of the digital linear phase filter is set to a frequency above the fundamental respiratory rate and below the fundamental heart rate. The upper limit, on the other hand, can be set to reduce electrical noise from the mains. Thus, the IPG's front-end electronic circuitry may be configured to filter the pressure signal with a lower cutoff frequency between 0.75 Hz-1.75 Hz, and with an upper cutoff frequency between 20 Hz-30 Hz. The pressure signal either represents the IJV or CCA pressure based on the patient's position. A preferred sampling rate is 200 Hz.

Alternatively, a kinematic sensor (e.g. the triaxial accelerometer of the tilt sensor, or another accelerometer) is encapsulated in the body of the lead 200 close to the distal lead end, allowing extraction of the IJV and CCA pressure waveforms via signal processing of the tilt (static) and kinematic responses of such sensors.

Morphological filters can also be implemented in the IPG's embedded electronic circuitry to track changes in the IJV and CCA pressure waveforms. The parameters of these filters may be adjusted following implantation. Deviations from the original waveforms over time can indicate heart complications that may occur with the progression of the patient's condition. Further, changes in the Pulse Transit Time (PTT) 602 (FIG. 6), i.e. the delay between R-wave detection and the peak of the CCA pressure waveform, can be used to determine arterial stiffness and to monitor arterial blood pressure. PTT trending analysis can be used to assess disease progression.

The tilt sensor can also be used to extract sleeping angle patterns. A decrease in the patient's sleeping angle may indicate an improvement in the patient's condition, as patients with CHF tend to sleep with several pillows due to breathing difficulties as their lungs fill with fluid. Furthermore, the kinematic sensor can be used to determine the Reflected Wave Transit Time (RWTT) of the CCA pulse wave, which is the temporal difference between the incident and reflected wave at the same position. It has been shown in vivo that the RWTT has high correlation with systolic blood pressure, and thus it can be used for systolic blood pressure estimation.

The IPG can be wirelessly programmed by an external Programmer via a MICS-band link (or equivalent). It can also communicate with a bedside Patient Messenger via a similar link. Arrhythmia detection, blood pressure waveform changes, and the other relevant diagnostic parameters described herein can be transmitted to the bedside Patient Messenger, which can alert a Home Monitoring/Remote Programming Center if medical attention is required.

Figure 7:
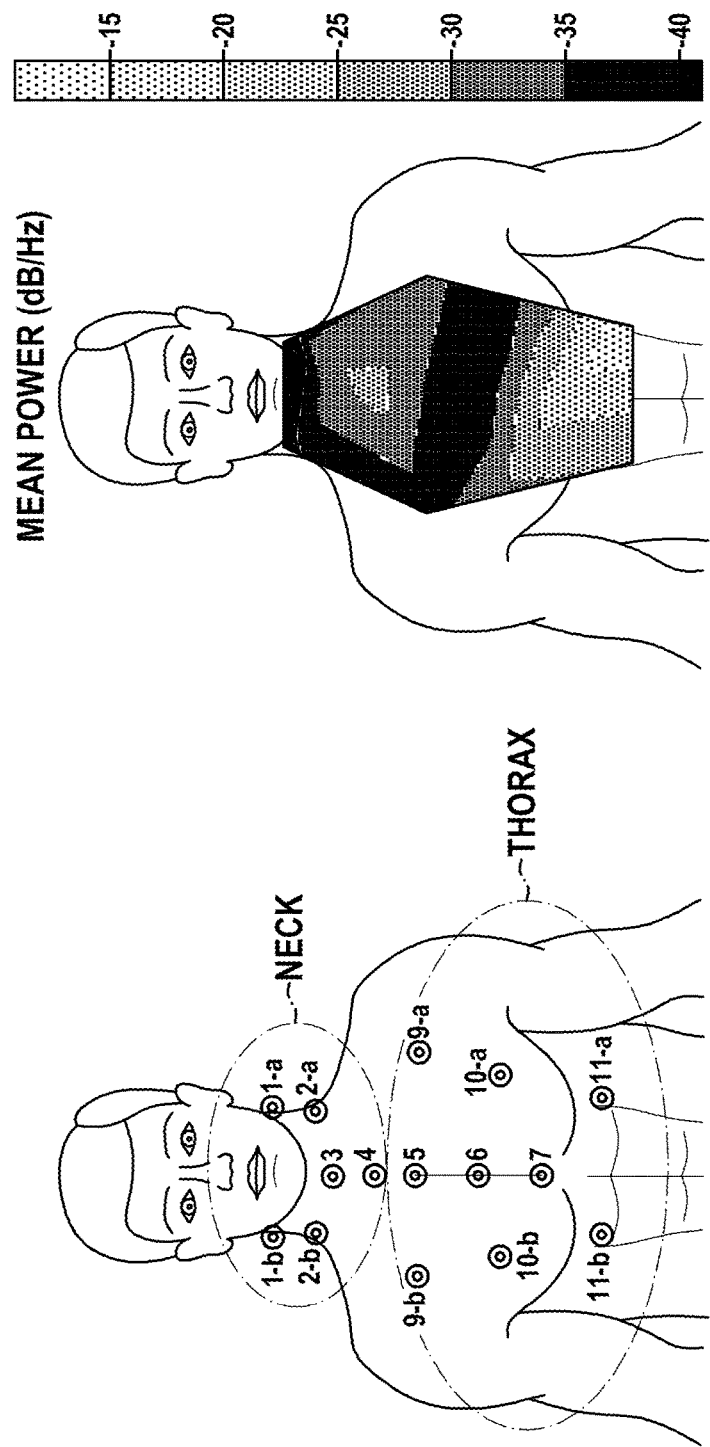
FIG. 7 shows that the kinematic mean power at the implantable pulse generator implant sites (somewhere between 9-a and 10-a) is 20 dB below the maximum measured at the ideal chest position (at or near 11-a)

The kinematic sensor may be configured to also or alternatively derive a Respiration Effort Signal (REFFS). REFFS may be obtained by first band-pass filtering the kinematic sensor response between 0.1 Hz and 0.5 Hz. FIG. 7 shows that the mean power at the suggested kinematic sensor implant sites (i.e., somewhere around 9-*b*, 10-*b* if in the IPG, and around 1-*b*, 2-*b* if in the lead 200) is 20 dB below the maximum measured at the ideal chest position (around 11-*b*). Given the reduced signal-to-noise ratio, signal processing for REFFS extraction preferably involves a morphological filter algorithm. Signal processing for REFFS extraction can also be based on discrete wavelet transforms. In this case, combining signals from both the kinematic sensor and ff-EGM may increase the event classification accuracy compared to use of only the kinematic sensor signal. U.S. Pat. No. 8,419,645 B2 describes how morphological operators can be utilized to determine respiration parameters from a transthoracic impedance signal. These operators can be applied in an analogous manner to extract REFFS, and also IJV and CCA pressure waveforms, from a kinematic sensor.

Figure 8:
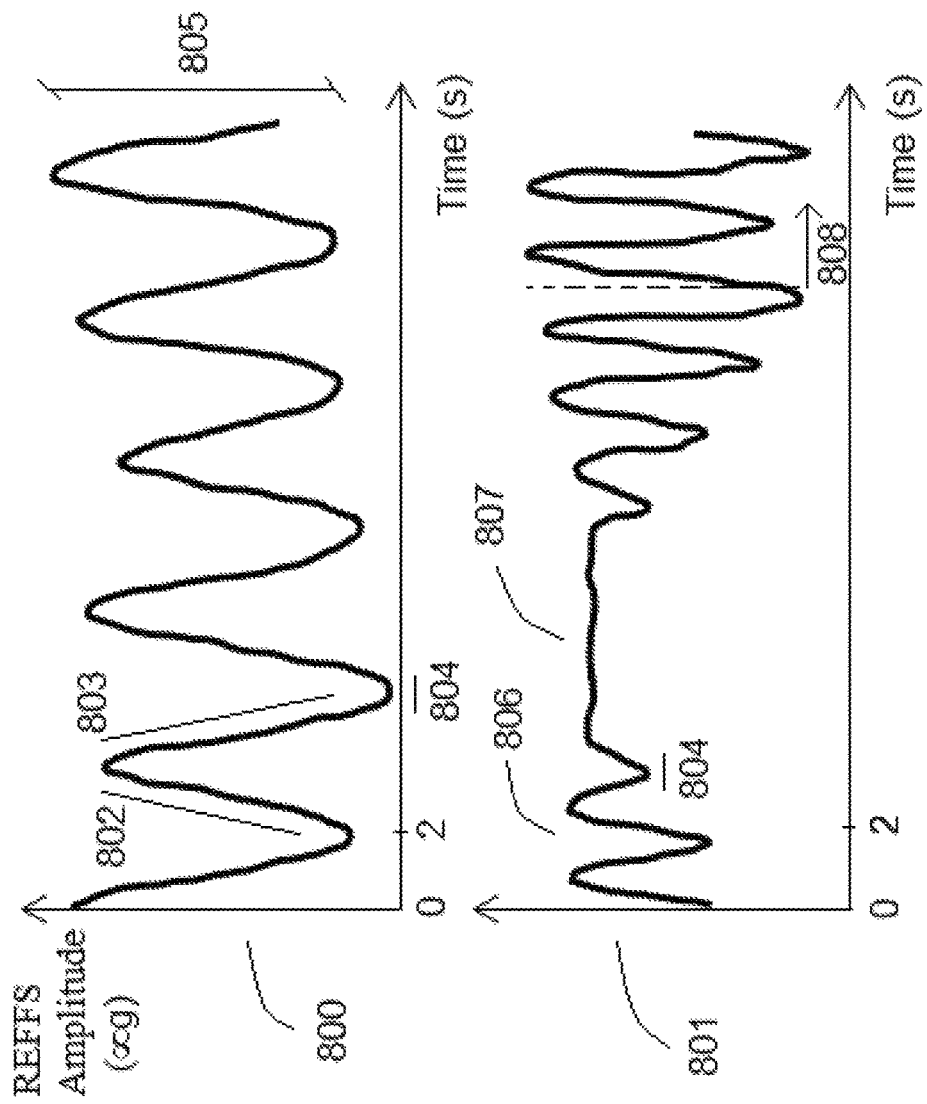
FIG. 8 illustrates the respiration effort signal (REFFS) in a CHF patient with CSA.

Given the proximity of the phrenic nerve 105.1 (see FIG. 4), VNS pulses are preferably delivered in anticipation of a physiological event in the respiration pattern that can be predicted from REFFS. The REFFS amplitude is proportional to gravity acceleration ($\propto g$). As shown in the top of FIG. 8, normal breathing 800 alternates periods of inspiration 802 and expiration 803, with a brief pause in between 804, and with a minimum REFFS amplitude 805 being indicative of the patient's normal tidal volume.

Preferably, the delivery of the VNS train of pulses begins during the breathing pause 504. Given the delay between phrenic nerve stimulation (PhrNS) and diaphragm muscle contraction, this feed-forward control permits any VNS stimulation spillage to the phrenic nerve 105.1 (should it happen) to occur at an inspiration phase 802, thereby providing breathing assistance for the patient. VNS may be duty cycled and delivered intermittently, i.e., once every n breathing pauses 804, and may only be active during programmable daily session times.

As mentioned before, half of the CHF patient population suffers from central sleep apnea (CSA). The REFFS in a CHF patient with CSA alternates between two breathing characteristics during sleep (see bottom of FIG. 8), known as the Cheyne-Stokes respiration pattern 801.

For this population of patients, both VNS and PhrNS can be delivered as required by (for example) lead 200 (FIG. 2). VNS can be performed, for example, between electrodes 201.1 (cathode) and 201.3 (anode), whereas PhrNS can be performed (for example) between electrodes 201.2 (cathode) and 201.3 (anode). The stimulation is preferably current-based and VNS and PhrNS are not delivered simultaneously, i.e., VNS is programmed for delivery during normal breathing, and is interrupted when hypopnea or apnea events are detected from REFFS as explained below.

Referring again to FIG. 8, when the normal REFFS excursion 805 drops, a detection algorithm in the IPG may determine that a hypopnea event 806 is occurring, and PhrNS therapy may be started during the next breathing pause 804. To directly detect apnea events 807, a programmable timer 808 can measure from the onset of each inspiration period 802 (once normal breathing 800 is established), and PhrNS therapy can be started if the start of the following inspiration period 802 cannot be determined from REFFS before the timer 808 elapses.

VNS and PhrNS are preferably delivered multiplexed in time, and with PhrNS having priority over VNS, i.e., if VNS is being delivered and either a hypopnea 806 or an apnea 807 condition is detected from REFFS, then VNS may be aborted until PhrNS restores normal breathing 800.

PhrNS therapy preferably consists of a programmable train of pulses having a frequency similar to that of VNS (preferably tens of Hz). However, each train may include a ramp-up phase, wherein both charge injected per pulse and frequency between pulses is ramped up, and a ramp-down phase. This type of pulse train allows for a more natural recruitment of the diaphragm. Once PhrNS has restored REFFS to the amplitude 805, stimulation is stopped and REFFS monitoring is continued.

The IPG for combined CHF-CSA may alternatively or additionally operate in a stimulation mode where REFFS is also used as feed-forward parameter for the delivery of PhrNS therapy. This mode may be triggered by a patient or clinician (e.g., by approaching a magnet near the implanted IPG), for example, if the patient is hospitalized and placed on mechanical ventilation. In such a situation, PhrNS may minimize diaphragm atrophy, and may therefore accelerate the patient's weaning off of ventilation. This mode does not prevent VNS therapy from being delivered, as VNS therapy can be time-multiplexed with PhrNS.

It should be appreciated that VNS and PhrNS may be provided using different combinations of veins, leads, and implant sites. As one example, more than one lead 200 may be implanted for VNS and PhrNS. As another example, looking to FIG. 3, the lead 200 may be implanted through the left subclavian vein (LSCV) to travel through the lumen of the left and right brachiocephalic veins (LBCV and RBCV respectively), and up the lumen of the RIJV for implantation. The IPG may then be implanted in the left side of the patient's chest, which allows for a larger ff-EGM signal.

Figure 9:
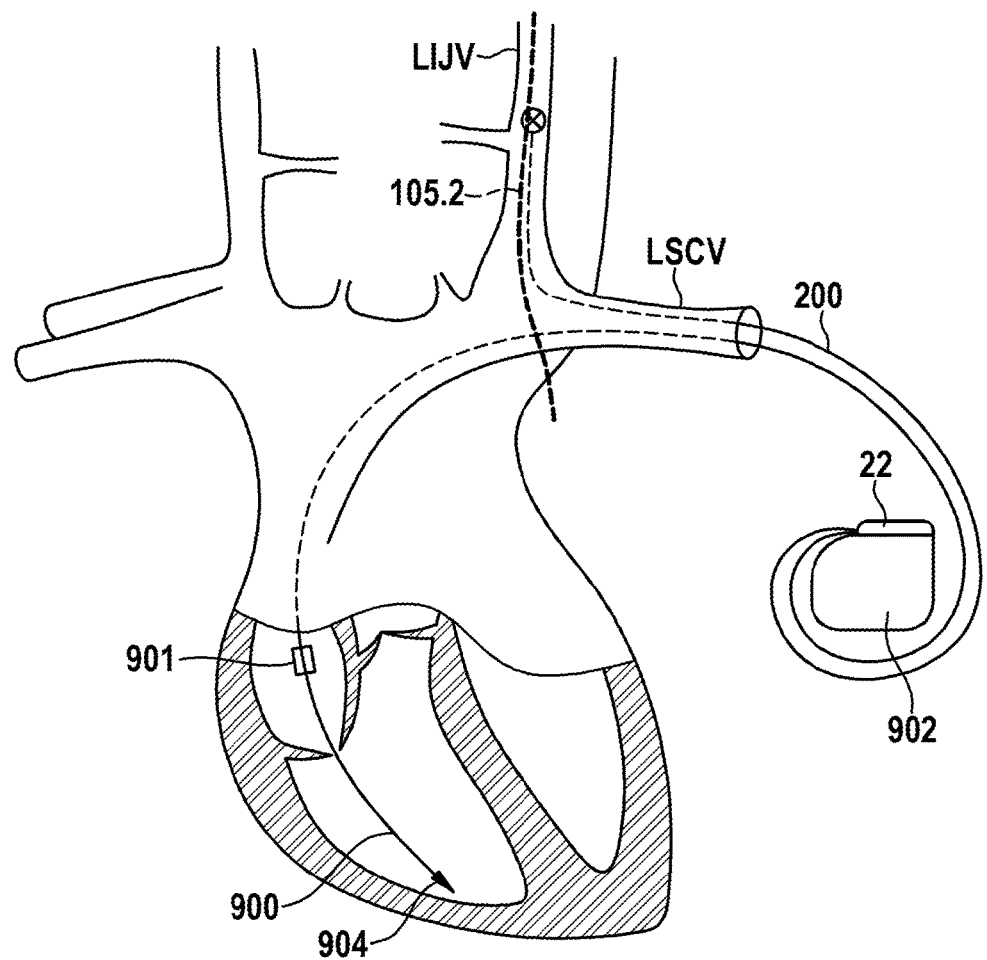
FIG. 9 illustrates an implantable pulse generator having both a nerve stimulation lead and a right ventricular lead with at least a floating atrial contact.

As yet another example shown in FIG. 9, the lead 200 is inserted through the LSCV to travel up the lumen of the LIJV, and is anchored in the vicinity of the left vagus nerve 105.2, which runs posteriorly to the LIJV. In addition to the lead 200, a right ventricular lead 900 is implanted, and the IPG 902 incorporates VDD pacemaker circuitry in addition to electronics for nerve stimulation. The right ventricular lead 900 includes a floating atrial electrode 901, as well as a ventricular electrode at the distal end of lead 900 for delivering ventricular stimulation pulses and/or sensing ventricular events.

The lead 900 allows monitoring for paroxysmal or persistent atrial fibrillation (AF), drug efficacy in AF treatment, and/or PR interval for autonomic tone, while also allowing delivery of nerve stimulation synchronized with atrial or ventricular events. It also allows monitoring of changes to the AV delay caused by stimulation of the left vagus nerve 105.2. Ventricular pacing may further be provided as a safety feature.

The invention can also be useful for assisting/controlling breathing in patients with partial or complete respiratory insufficiency, e.g. chronic obstructive pulmonary disease (COPD) or quadriplegia. For quadriplegia, bilateral leads 200 are implanted, for example, through the LSCV and anchored in the vicinity of phrenic nerves 105.1 and 105.2. Rhythmic application of electrical stimulation to the diaphragm via PhrNS results in respiration for patients who would otherwise be dependent on a mechanical ventilator.

FIG. 10 is a schematic diagram of components of the IPG 902 of FIG. 9. As seen in FIG. 9, the IPG 902 includes a case (IPG case) 20 and a header 22 for connection of leads 200 and 900. The header 22 includes a number of connectors 24, 26, 28, 30, 32 and 34 (FIG. 10) that can electrically connect to connectors of the stimulation lead 200. Thus, an electric connection can be made between the connectors 24, 26, 28, 30, 32 and 34 and the electrodes 201 (e.g., in FIG. 5) of the stimulation lead 200, and the electrodes 901, 904 of the pacing lead 900 (FIG. 9).

Within the IPG case 20, one or more stimulation units 36, 38, 40, 42, 44 and 46 are respectively electrically connected to the connectors 24, 26, 28, 30, 32 and 34, and are configured to generate stimulation pulses and to deliver the pulses via a respective connector 24, 26, 28, 30, 32 and 34. However, instead of having one stimulation unit 36 to 46 for each connector 24 to 34 (and thus for each electrode 201 of lead 200 in FIG. 5), one stimulation unit and a switch matrix can be provided, whereby the switch matrix allows delivery of stimulation pulses via selected connectors (and thus via selected electrodes 201 of lead 200). In another version of the illustrated arrangement, all electrodes 201 of lead 200 are switched in parallel to each other, and thus only one connector and one stimulation unit is needed.

In the version of FIG. 10, each stimulation unit 36, 38, 40, 42, 44 and 46 is connected to and controlled by a control unit 50. The control unit 50 controls generation and triggers delivery of stimulation pulses by the stimulation units 36, 38, 40, 42, 44 and 46. The stimulation pulses to be generated and triggered by each stimulation unit 36, 38, 40, 42, 44 and 46 are tailored for vagus and phrenic nerve stimulation, and/or cardiac stimulation.

The control unit 50 is further connected to a time base generator 52 that supplies a time base to the control unit 50.

The IPG further includes a kinematic sensor unit 54, preferably a triaxial accelerometer for sensing movements of the IPG 902 in three spatial dimensions, which delivers a position/motion signal to control unit 50. The kinematic sensor unit 54 is used as a tilt sensor, and also for generating the REFFS.

The control unit 50 is also connected to a far-field electrogram (ff-EGM) sensing unit 56 configured to generate a ff-EGM signal representing a far-field electrogram 604 (see FIG. 6) when no pacing lead 900 is utilized. (If a pacing lead 900 is utilized, the sensing unit 56 would then simply record EGM.) To record ff-EGM, the ff-EGM sensing unit 56 is connected to at least one of connectors 24 to 34, and thus to one of the electrodes 201 of lead 200. Another input of the ff-EGM sensing unit 56 is connected to the IPG case 20. Thus, the ff-EGM sensing unit 56 can sense voltages between an electrode 107 and the IPG case 20 that result from electric potentials caused by the patient's heart activity. The far-field electrogram (ff-EGM) sensing unit 56 is configured to supply a ff-EGM signal to the control unit 50 wherein the ff-EGM signal represents the patient's heart activity. The patient's heart rate and other parameters can be determined from the ff-EGM signal.

The control unit 50 is further connected to an impedance measuring unit 60 that includes a programmable current source 62 for generating and delivering biphasic impedance measuring pulses. The current source 62 may be electrically connected to the IPG case 20 and to at least one of the connectors 24 to 34, and thus to the lead electrodes 201.1 and 201.2 on lead 200 (see FIG. 5). The impedance measurement unit 60 further includes a voltage sensing unit 64 configured to measure a voltage difference between lead electrodes 201.3 and either 201.1 or 201.2 (in the version of the invention shown in FIG. 5) in response to delivery of current pulses by the current source 62. The current source 62 and the voltage sensing unit 64 are connected to an impedance determination unit 66 of the impedance measurement unit 60. The impedance determination unit 66 is configured to generate an impedance signal depending on the voltages measured by voltage sensing unit 64, and to supply the impedance signal to the control unit 50. The impedance signal generated by the impedance measurement unit 60 allows indirect determination of the combined pressure waveforms of both the IJV and the CCA by means of impedance plethysmography utilizing lead electrode 201.3 and either of electrodes 201.1 and 201.2 on lead 200. It should be understood that the lead 200 may include further electrodes for impedance measurement.

The control unit 50 may be further connected to a memory unit 70 that may serve to store signals recorded by control unit 50, and/or programs that control the operation of control unit 50.

In order to wirelessly communicate recorded signals to an external device or to receive program instructions, a telemetry unit 72 is also connected to the control unit 50.

The invention is not intended to be limited to the exemplary versions discussed above, but rather is intended to be limited only by the claims set out below. Thus, the invention encompasses all different versions that fall literally or equivalently within the scope of these claims.

What is claimed is:

1. An implantable stimulation system including:
   a. a pulse generator,
   b. an implantable lead (200) extending:
      (1) between:
         (a) a proximal end (301) connected to the pulse generator, and
         (b) a distal end:
            i. including an expandable member (202):
               A. formed of elastic electrically insulating material, and
               B. bearing a stimulation electrode (201.1, 201.2) electrically connected to the pulse generator,
            ii. wherein the expandable member (202) is configured to expand from:
               A. a compact state wherein the expandable member (202) is closely adjacent the lead (200), and
               B. an expanded state wherein the expandable member (202) laterally extends from the lead (200);
      (2) within a vessel (103.1) having a vessel wall, and
      (3) through the vessel wall with the expandable member (202) in the expanded state outside the vessel.

2. The implantable stimulation system of claim 1 wherein the lead further includes a lead electrode (201.3) thereon spaced from the expandable member (202) and situated within the vessel.

3. The implantable stimulation system of claim 1 wherein the expandable member (202) in the expanded state includes a distally facing front area whereupon the electrode (201.1, 201.2) is situated.

4. The implantable stimulation system of claim 1 wherein the lead (200) includes a lead electrode (201.3) thereon, with the lead electrode (201.3) being spaced from the distal end of the lead (200) by more than 0.5 cm.

5. The implantable stimulation system of claim 1 wherein the pulse generator:
   a. includes an electrically conductive case (20), and
   b. is configured to perform electrical impedance plethysmography via the electrode and the case (20).

6. The implantable stimulation system of claim 1 wherein the pulse generator includes a kinematic sensor (54) configured to generate a tilt signal indicative of inclination.

7. The implantable stimulation system of claim 1 wherein the pulse generator:
   a. includes a kinematic sensor (54), and
   b. is configured to generate a respiration effort signal (REFFS) from an output of the kinematic sensor (54).

8. The implantable stimulation system of claim 1 wherein the pulse generator:
   a. includes an electrically conductive case (20), and
   b. is configured to obtain a far-field electrogram via:
      (1) at least one of:
         (a) the electrode (201.1, 201.2), or
         (b) a lead electrode (201.3) spaced from the electrode (201.1, 201.2) on the lead (200), and
      (2) the case (20).

9. The implantable stimulation system of claim 8 wherein the pulse generator is configured to record vascular pressure waveforms depending on the tilt signal and the far field electrogram.

10. An implantable stimulation system including:
    a. a pulse generator,
    b. an implantable lead (200) extending between:
       (1) a proximal end (301) connected to the pulse generator, and
       (2) a distal end:
          (a) including an expandable member (202):
             i. formed of elastic electrically insulating material, and
             ii. bearing a stimulation electrode (201.1, 201.2) electrically connected to the pulse generator,
          (b) wherein the expandable member (202) is configured to expand from:
             i. a compact state wherein the expandable member (202) is closely adjacent the lead (200), and
             ii. an expanded state wherein the expandable member (202) laterally extends from the lead (200),
    wherein the pulse generator is configured to deliver stimulation pulses for at least one of:
    I. vagus nerve stimulation (VNS), and
    II. phrenic nerve stimulation (PhrNS),
    via the electrode (201.1, 201.2).

11. The implantable stimulation system of claim 10 wherein the pulse generator is configured to:
    a. generate a respiration effort signal (REFFS), and
    b. deliver VNS and/or PhrNS depending on the REFFS.

12. The implantable stimulation system of claim 1:
    a. further including a cardiac lead (900),
    b. wherein the pulse generator (902) is further configured to:
       (1) sense cardiac activity, and
       (2) deliver cardiac stimulation pulses via the cardiac lead (900).

13. The implantable stimulation system of claim 1 wherein the pulse generator is configured to deliver stimulation pulses for at least one of:
    a. vagus nerve stimulation (VNS), and
    b. phrenic nerve stimulation (PhrNS),
    via the electrode (201.1, 201.2).

14. The implantable stimulation system of claim 13 wherein the pulse generator is configured to:
    a. generate a respiration effort signal (REFFS), and
    b. deliver VNS and/or PhrNS depending on the REFFS.

15. The implantable stimulation system of claim 1:
    a. further including a cardiac lead (900),
    b. wherein the pulse generator (902) is further configured to:
       (1) sense cardiac activity, and (2) deliver cardiac stimulation pulses via the cardiac lead (900).

16. The implantable stimulation system of claim 15 wherein the pulse generator (902) is configured to:
 a. detect at least one of:
  (1) atrial fibrillation (AF), and
  (2) PR interval,
  via the cardiac lead (900), and
 b. deliver nerve stimulation pulses via the electrode (201.1, 201.2) in synchrony with cardiac activity.

17. An implantable stimulation system including:
 a. a pulse generator,
 b. an implantable lead (200) extending between:
  (1) a proximal end (301) connected to the pulse generator, and
  (2) a distal end:
   (a) including an expandable member (202):
    i. formed of elastic electrically insulating material, and
    ii. bearing a stimulation electrode (201.1, 201.2) electrically connected to the pulse generator,
   (b) wherein the expandable member (202) is configured to expand from:
    i. a compact state wherein the expandable member (202) is closely adjacent the lead (200), and
    ii. an expanded state wherein the expandable member (202) laterally extends from the lead (200),
 c. a cardiac lead (900),
 wherein the pulse generator (902) is configured to:
  a. detect at least one of:
   (1) atrial fibrillation (AF), and
   (2) PR interval,
   via the cardiac lead (900), and
  b. deliver:
   (1) cardiac stimulation pulses via the cardiac lead (900), and
   (2) nerve stimulation pulses via the electrode (201.1, 201.2) in synchrony with cardiac activity.

18. The implantable stimulation system of claim 17 wherein the pulse generator is configured to deliver stimulation pulses for at least one of:
 a. vagus nerve stimulation (VNS), and
 b. phrenic nerve stimulation (PhrNS),
 via the electrode (201.1, 201.2).

19. The implantable stimulation system of claim 18 wherein the pulse generator is configured to:
 a. generate a respiration effort signal (REFFS), and
 b. deliver VNS and/or PhrNS depending on the REFFS.

* * * * *